Figure 1:
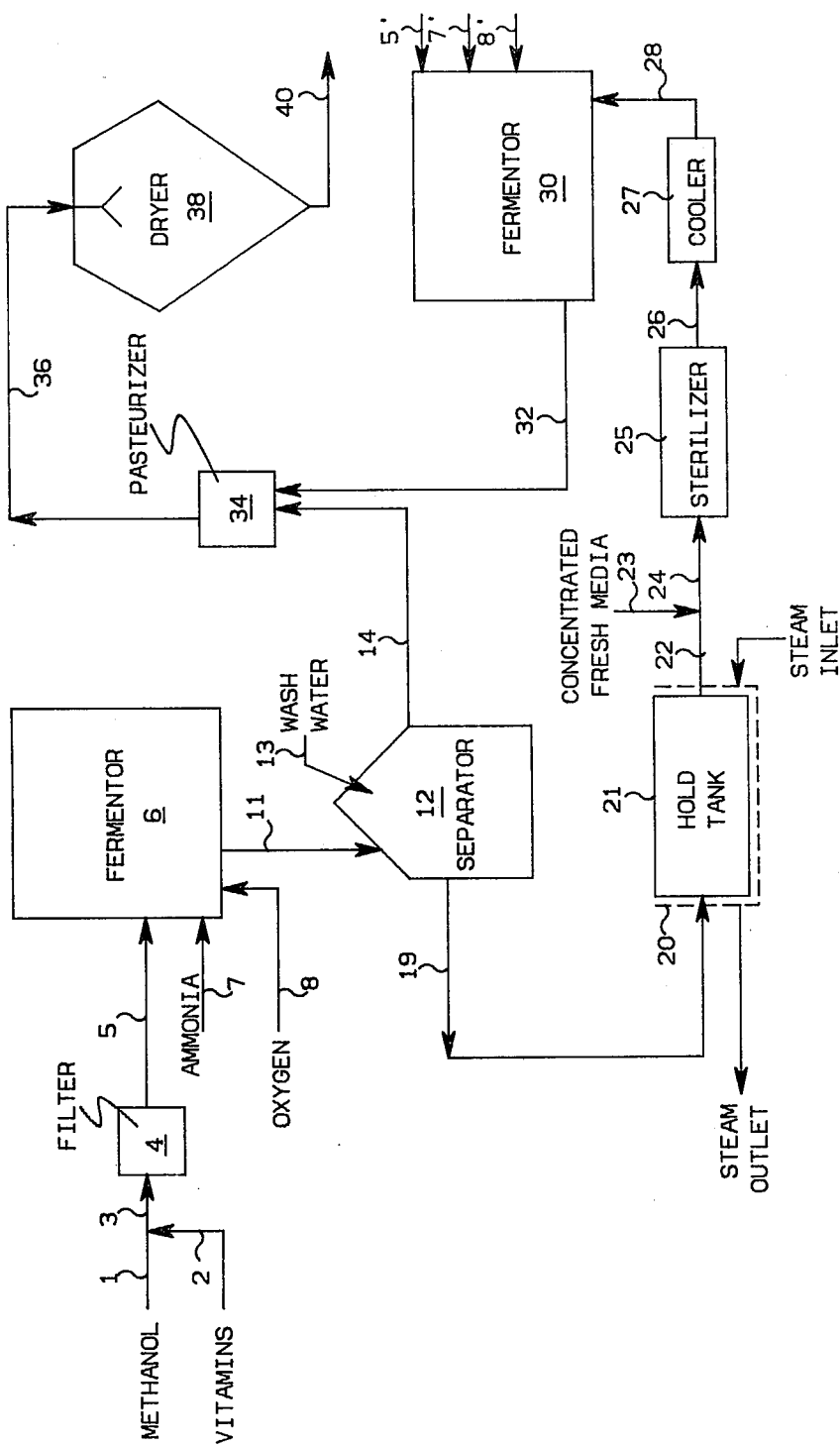

United States Patent [19]

Malick et al.

[11] 4,439,523

[45] Mar. 27, 1984

[54] PRODUCTION OF SINGLE CELL PROTEIN MATERIAL

[75] Inventors: Emil A. Malick; John W. Vanderveen; Donald O. Hitzman; Eugene H. Wegner, all of Bartlesville, Okla.

[73] Assignee: Phillips Petroleum Company, Bartlesville, Okla.

[21] Appl. No.: 280,963

[22] Filed: Jul. 7, 1981

[51] Int. Cl.$^3$ .......................... C12N 1/00; C12N 1/02
[52] U.S. Cl. .................................. 435/243; 435/255; 435/261
[58] Field of Search ............... 435/243, 247, 248, 819, 435/255, 261; 426/53, 54

[56] References Cited

U.S. PATENT DOCUMENTS

| | | | |
|---|---|---|---|
| 3,489,648 | 1/1970 | Wegner | 435/248 |
| 3,767,534 | 10/1973 | Miura | 435/243 X |
| 3,793,153 | 2/1974 | Miura | 435/255 X |
| 3,865,691 | 2/1975 | Ridgway, Jr. et al. | 435/247 |
| 3,982,998 | 9/1976 | Hitzman et al. | 435/247 X |
| 4,019,962 | 4/1977 | Allen et al. | 435/247 X |

*Primary Examiner*—Robert A. Yoncoskie

[57] ABSTRACT

There is disclosed disposal of effluent from a low cell density fermentation process by using such effluent as at least a portion of the feed material to a high cell density fermentation process. A stream containing microbial cells from the high cell density fermentation process is subjected to direct drying.

6 Claims, 2 Drawing Figures

FIG. I

PRODUCTION OF SINGLE CELL PROTEIN MATERIAL

This invention relates to a process for cultivating microorganisms. In another respect, the invention relates to continuous cultivation of microorganisms. In yet another aspect, the invention relates to continuously cultivating microorganisms wherein a low cell density ferment stream is suitably treated to kill the microorganism cells, and then supplied to a high cell density fermentation vessel as part of the nutrient medium therefor. In yet another aspect the invention relates to continuously cultivating microorganisms wherein a ferment stream is suitably treated to separate cells from the fermentation broth, and the residual fermentation liquor is then supplied to high cell density fermentation vessel as part of the nutrient medium therefor.

Efforts to relieve world wide shortages of protein have included production of single cell protein (SCP) by growth of one or another of a variety of microorganisms on various substrates under aerobic aqueous fermentation conditions. The term SCP is variously employed to designate a predominantly proteinaceous product from which nonprotein constituents for example, cell wall materials, lipids, and the like, have been largely removed as well as the whole cell product which would, of course, include such as cell wall materials, lipids and the like. Hydrocarbon derived substrates suitable for production of SCP are preferably water soluble, readily available, relatively cheap, uniform, and safe. The economics of such fermentation systems can be enhanced by separating the cells from an aqueous cellular suspension and recycling the aqueous liquor to a fermentation process. Further enhancement of fermentation economics can be realized by conducting the fermentation at high cell densities, so that separation of SCP products from the fermentation liquor is not required. When grown at high cell density the fermentation effluent can be subjected directly to drying conditions such as spray drying or drum drying, thereby substantially eliminating the formation of an effluent waste stream.

Problems can be encountered in the use of recycle systems including the accumulation of inhibitory metabolic by-products and growth of contaminating microorganisms in the recycled liquor. The growth of contaminating microorganisms can result in the synthesis of metabolic by-products which are inhibitory to the growth of the selected culture microorganisms or even in the synthesis of toxic compounds that could contaminate the final product. Moreover, since the strain of culture microorganisms utilized is usually selected for specific characteristics depending upon its ultimate use, such as, for example, high protein content and amino acid balance for animal food use, it is important that growth of contaminating microorganisms be controlled. Finally, such recycle systems can be efficacious in reducing the amount of waste fluid which must be disposed of in a manner noninjurious to environmental concerns.

Accordingly an object of the instant invention is to provide a method and apparatus for conducting high density single cell protein production which minimizes problems associated with waste liquor disposal. Another object is to provide a method and apparatus for conducting single cell protein production which utilizes nutrient-containing effluent liquor separated from a first single cell protein fermentor as at least a portion of the nutrient-containing feed for a second fermentor which is operated at high cell density. Yet another object is to provide a method and apparatus for fermentation in which a microorganism, regardless of productivity, can be isolated and recovered in a simplified manner as though high cell density growth conditions were present. A further object is to provide a method and apparatus for the production of a quality mixed protein product.

In accordance with the invention, a method and apparatus are provided for conducting single cell protein production. A microorganism is fermented in a first fermentor of a fermentation process. A portion of the ferment is removed from the fermentor as an effluent stream which, in a first embodiment of the invention is passed to a separator which separates the effluent stream into two streams, one having a higher cell density than the other. In this embodiment, the stream having a lower cell density can then be passed to a tank which in various specific configurations within the scope of the invention can be designated a hold tank, surge tank, make-up tank or otherwise. Irrespective of the designation or subsidiary functions which might be suggested by the designation, at least a portion of the lower cell density fluid is maintained in such a hold tank under nonsterilizing conditions inhibitory to cell growth. At least a portion of the thus held fluid can then be fortified with additional nutrients, sterilized, cooled and otherwise be appropriately conditioned to be introduced into a second fermentor, wherein a second microorganism is fermented in a high cell density fermentation process.

In an alternate embodiment, a portion of the ferment is removed from the first fermentor as an effluent stream which is pasteurized to kill the microorganism cells therein. This stream is passed optionally to a hold tank, surge tank, make-up tank or otherwise. At least a portion of the thus held fluid can then be fortified with additional nutrients, sterilized, cooled, and can be otherwise appropriately conditioned to be introduced into a second fermentor, wherein a second microorganism is fermented in a high cell density process.

In various embodiments of this invention, additional sterilized and cooled nutrients are added to the pasteurized effluent stream of the first fermentor, and introduced directly to the second fermentor, wherein a second microorganism is fermented in a high cell density process.

As required, detailed embodiments and illustrative examples of the instant invention are disclosed herein. It is to be understood, however, that these specific embodiments and examples are merely illustrative of the invention which may be embodied in various forms. Therefore, such specific structural and functional details of such presently preferred embodiments as are disclosed herein are not to be interpreted as limiting but merely as a basis for the claims and as a representative basis for teaching one skilled in the art to variously employ the instant invention in any appropriate manner or structure.

In FIG. 1 there is schematically illustrated a fermentation process employing the invention.

Figure 2:
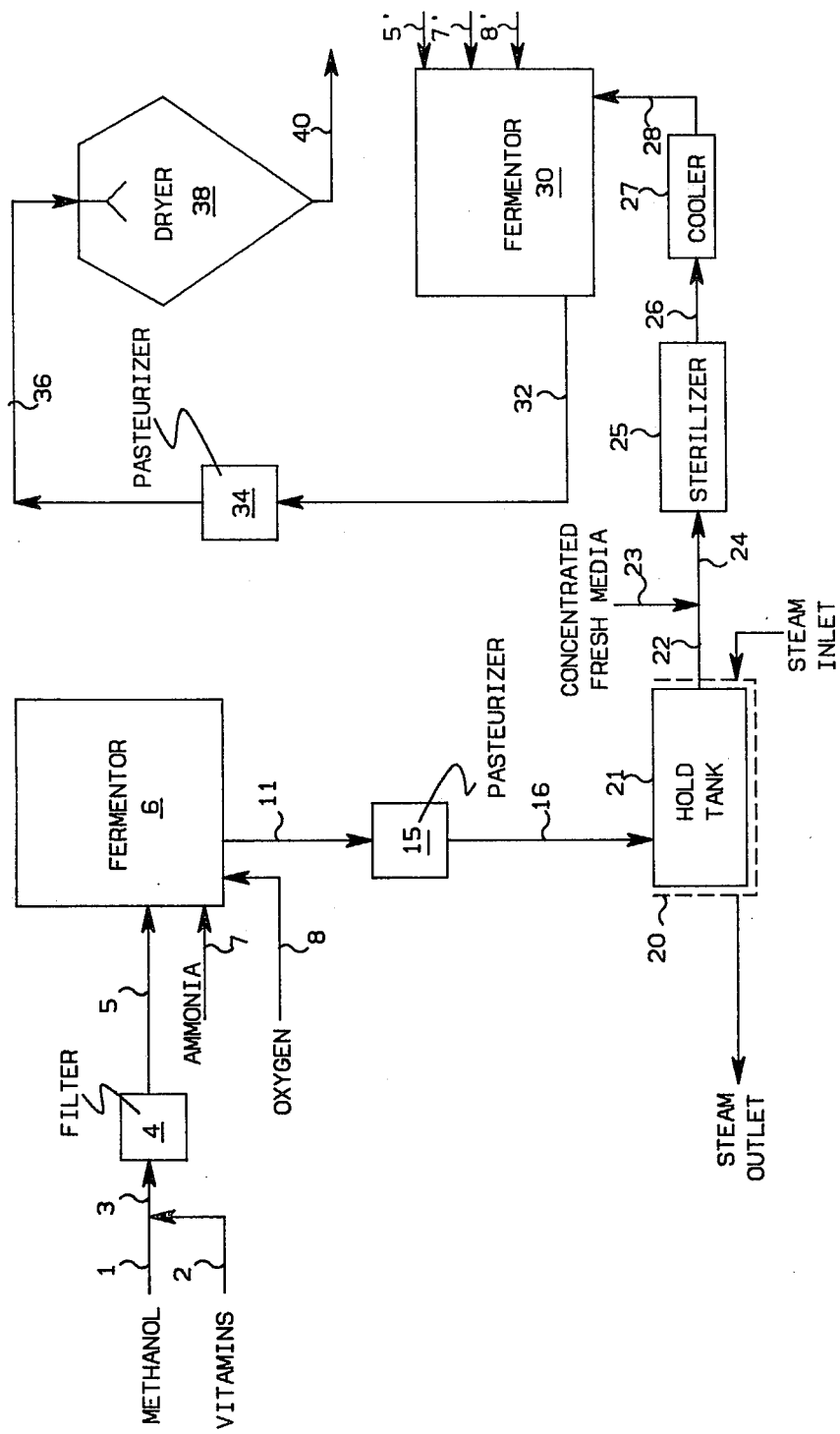

FIG. 2 is an alternative embodiment of the invention implemented using a similar fermentation process.

Referring now to the drawings in detail, in FIG. 1 a carbon and energy source stream 1, such as methanol, a micronutrient source stream 2, containing, for example, vitamins, biotin and thiamine in aqueous methanol solution, a nitrogenous compound source stream 7, such as ammonia, and an aeration stream containing utilizable oxygen 8 are employed in a first fermentor 6 which also receives microorganism culture inoculum and is operated under aerobic aqueous fermentation conditions to produce a cell rich ferment. In the illustrated embodiment, the feedstock stream 1 is mixed with a heat labile micronutrient source stream 2 to form combined stream 3. Stream 3 is then filtered through a filter 4, which can be, for example, a cartridge filter having pore sizes of 1 micron or less to provide a sterile carbon and energy source stream 5 containing heat labile micronutrient to be introduced into a fermentor 6.

At least a portion of the cell rich ferment is removed periodically, intervallically, or continuously from fermentor 6 in a fermentor SCP product stream 11 to a separator 12, such as a centrifuge. The separator 12 functions to separate stream 11 into a concentrated SCP product stream 14 having a generally higher cell density than stream 11 and a separator effluent stream 19 having a generally lower cell density than stream 11, for example, by centrifugation which may employ at least one fresh water wash utilizing wash water stream 13. At least a portion of separator effluent stream 19 is held in a hold tank 21 where it is maintained, for example, by a steam jacket 20 as shown in FIG. 1, at a temperature effective to inhibit growth of microorganisms. At least a portion of the thus held effluent can be removed from the hold tank in recycle stream 22 and combined with medium enhancing stream 23 containing concentrated fresh media as hereinafter described. The combined medium-enhanced recycle stream 24 is then sterilized in a sterilizer 25, such as a steam sterilizer, to produce a sterilized medium-enhanced recycle stream 26 which is then cooled in cooling means 27 such as a heat exchanger, to produce a cooled sterilized medium-enhanced recycle stream 28 suitable for introduction into the second fermentor as a complementary nutrient stream to streams 5', 7', and 8'. Streams 5', 7' and 8' correspond to streams 5, 7 and 8 respectively and are provided to the reactor 30 for the same purpose and effect as streams 5, 7, and 8 are provided to the reactor 6. The second fermenter 30 is operated at high cell density conditions to produce a high cell density SCP product stream 32. Concentrated SCP product streams 14 and 32 are pasteurized in a pasteurizir 34 to produce a pasteurized SCP product stream 36 from which liquid is removed in a dryer 38 to produce a dried SCP product 40 which may be further processed as required for use as an animal or human feed supplement.

In FIG. 2, a second embodiment of the invention is shown in which product stream 11 is introduced directly to a pasteurizer 15 to produce a pasteurized SCP product stream 16. At least a portion of pasteurized product stream 16 can be held in hold tank 21 which is fed to fermentor 30 as described hereinabove. Other features and reference numerals of FIG. 2 correspond to those of FIG. 1.

In a preferred embodiment of this invention, the fermentations are carried out with a straight chain alcohol. Such alcohols can generally have from 1 to 16 carbon atoms per molecule. This is referred to as the feedstock and is assimilable by the microorganism and supplies the carbon and energy for the microbial growth. Preferably the alcohol has from 1 to 6 carbon atoms per molecule and more preferably the alcohol will be either ethanol or methanol and most preferably, methanol because of price and availability. Examples of some suitable alcohols include methanol, ethanol, 1-propanol, 1-butanol, 1-octanol, 1-dodecanol, 1-hexadecanol, 2-propanol, 2-butanol, 2-hexanol and the like. Mixtures of alcohols can also be employed if desired.

Other substrates which can be used include carbohydrates. Usually the suitable carbohydrates have up to about 12 carbon atoms per molecule. Other oxygenated hydrocarbons such as ketones, aldehydes, acids, esters, and ethers are also suitable substrates and these usually have from 1 to about 20 carbon atoms per molecule. n-Paraffins having from 1 to about 20 carbon atoms per molecule can also be used as substrates.

The microorganism used in the fermentation process is one or more microorganism capable of assimilating one or more of the above alcohols as the source of carbon and energy in the growth or propagation of the microorganism. Suitable microorganisms can be selected from bacteria, yeast and fungi.

Suitable yeasts include species from the genera Candida, Hansenula, Torulopsis, Saccharomyces, Pichia, Debaryomyces, Lipomyces, Cryptococcus, Nematospora, and Brettanomyces. The preferred genera include Candida, Hansenula, Torulopsis, Pichia, and Saccharomyces. Examples of suitable species include:

| | |
|---|---|
| Candida boidinii | Torulopsis bolmii |
| Candida lipolytica | Torulopsis versatilis |
| Candida mycoderma | Torulopsis glabrata |
| Candida tropicalis | Torulopsis molishiana |
| Candida utilis | Torulopsis nemodendra |
| Candida stellatoidea | Torulopsis nitratophila |
| Candida robusta | Torulopsis pinus |
| Candida claussenii | Torulopsis sonorensis |
| Candida rugosa | Pichia farinosa |
| Brettanomyces petrophilium | Pichia polymorpha |
| Hansenula minuta | Pichia membranaefaciens |
| Hansenula saturnus | Pichia pinus |
| Hansenula californica | Pichia pastoris |
| Hansenula mrakii | Pichia trehalophila |
| Hansenula silvicola | Saccharomyces cerevisiae |
| Hansenula polymorpha | Saccharomyces fragilis |
| Hansenula wickerhamii | Saccharomyces rosei |
| Hansenula capsulata | Saccharomyces acidifaciens |
| Hansenula glucozmya | Saccharomvces elegans |
| Hansenula henricii | Saccharomvces rouxii |
| Hansenula nonfermentans | Saccharomyces lactis |
| Hansenula philodendra | Saccharomyces fractum |
| Torulopsis candida | |

Suitable bacteria include species from the genera Bacillus, Mycobacterium, Antinomyces, Nocardia, Pseudomonas, Methanomonas, Protaminobacter, Methylococcus, Arthrobacter, Methylomonas, Brevibacterium, Acetobacter, Micrococcus, Rhodopseudomonas, Corynebacterium, Rhodopseudomonas, Microbacterium, Achromobacter, Methylobacter, Methylosinus, and Methylocystis. preferred general include Bacillus, Pseudomonas, Protaminobacter, Micrococcus, Arthrobacter, Methylomonas, and Corynebacterium.

Examples of suitable species include:

| | |
|---|---|
| Bacillus subtilus | Corynebacterium viscosus |
| Bacillus cereus | Corynebacterium dioxydans |
| Bacillus aureus | Corynebacterium alkanum |
| Bacillus acidi | Micrococcus cerificans |
| Bacillus urici | Micrococcus rhodius |
| Bacillus coagulans | Arthrobacter rufescens |
| Bacillus mycoides | Arthrobacter parafficum |
| Bacillus circulans | Arthrobacter simplex |
| Bacillus megaterium | Arthrobacter citreus |
| Bacillus licheniformis | Methanomonas methanica |

| -continued |  |
|---|---|
| Pseudomonas methanolica | Methanomonas methanooxidans |
| Pseudomonas ligustri | Methylomonas agile |
| Pseudomonas orvilla | Methylomonas albus |
| Pseudomonas methanica | Methylomonas rubrum |
| Pseudomonas fluorescens | Methylomonas methanolica |
| Pseudomonas aeruginosa | Methylomonas rhodochrous |
| Pseudomonas oleovorans | Mycobacterium phlei |
| Pseudomonas putida | Mycobacterium brevicale |
| Pseudomonas boreopolis | Nocardia salmonicolor |
| Pseudomonas pyocyanea | Nocardia minimus |
| Pseudomonas methylphilus | Nocardia corallina |
| Pseudomonas brevis | Nocardia butanica |
| Pseudomonas acidovorans | Rhodopseudomonas capsulatus |
| Pseudomonas methanoloxidans | Microbacterium ammoniaphilum |
| Pseudomonas aerogenes | Archromobacter coagulans |
| Protaminobacter ruber | Brevibacterium butanicum |
| Corynebacterium simplex | Brevobacterium roseum |
| Cornybacterium hydrocarbooxydans | Brevibacterium flavum |
| Cornybacterium alkanum | Brevibacterium lactofermentum |
| Corynebacterium oleophilus | Brevibacterium paraffinolyticum |
| Cornybacterium hydrocarboclastus | Brevibacterium ketoglutamicum |
| Corynebacterium glutamicum | Brevibacterium insectiphilus |

The growth of the microorganism is sensitive to the operating temperature of the fermentor and each particular microorganism has an optimum temperature for growth. The broad temperature range employed for the fermentation process is generally from about 20° C. to 65° C. and more preferably between 30° C. and 60° C. The temperature selected will generally depend upon the microorganism employed in the process since each organism will have a somewhat different temperature/growth rate relationship.

In the practice of the present invention, a suitable nutrient medium is supplied to the first fermentor 6 by introducing a fresh media stream and supplied to the second fermentor 30 by introducing a concentrated fresh media stream 23 into the fermentor. Nutrients to be provided are selected from assimilable sources of nitrogen, phosphorus, magnesium, calcium, potassium, sulfur and sodium as well as trace quantities of copper, manganese, molybdenum, zinc, iron, boron, iodine, cobalt, and selenium. The relative amounts of the above nutrients can vary depending on the microorganism selected for the process. In addition, the nutrient medium can also contain vitamins when their presence is known to be desirable for the propagation of certain microorganisms. For example, many yeasts appear to require the presence of one or both of the vitamins, biotin and thiamine for their proper propagation. A typical composition of a suitable nutrient medium is as given below:

| One Liter Aqueous Solution | |
|---|---|
| Component | Amount |
| $H_3PO_4$ (85%) | 2.0 mL |
| KCl | 1.0 g |
| $MgSO_4.7H_2O$ | 1.5 g |
| $CaCl_2.2H_2O$ | 0.2 g |
| NaCl | 0.1 g |
| Trace Mineral Solution | 5.0 mL |

The trace mineral solution as listed in the above recipe is formulated as given in the recipe below:

| One Liter Aqueous Solution (Trace Mineral Solution) | |
|---|---|
| Component | Amount |
| $CuSO_4.5H_2O$ | 0.06 g |
| KI | 0.08 g |
| $FeCl_2.6H_2O$ | 4.80 g |
| $MnSO_4.H_2O$ | 0.30 g |
| $Na_2MoO_4.2H_2O$ | 0.20 g |
| $ZnSO_4.7H_2O$ | 2.00 g |
| $H_3BO_3$ | 0.02 g |

When a fermentor such as the fermentor 30 is operated under high cell density conditions, the nutrient medium provided must contain appropriate nutrient levels to support high density cell growth. A typical composition of a suitable nutrient medium for high cell density fermentation is as given below:

| One Liter Aqueous Solution | |
|---|---|
| Component | Amount |
| $H_3PO_4$(75%) | 23.8 mL |
| $CaSO_4.2H_2O$ | 0.9 g. |
| $K_2SO_4$ | 14.3 g. |
| $MgSO_4.7H_2O$ | 11.7 g. |
| KOH (85%) | 3.9 g. |
| Trace Mineral Solution | 5.0 mL |

| One Liter Aqueous Solution (Trace Mineral Solution) | |
|---|---|
| Component | Amount |
| $FeSO_4.7H_2O$ | 50.7 g. |
| $CuSO_4.5H_2O$ | 4.7 g. |
| $ZnSO_4.7H_2O$ | 15.6 g. |
| $MnSO_4.H_2O$ | 2.3 g. |
| Biotin | 0.032 g. |

The source of nitrogen for the fermentor can be any suitable organic or inorganic nitrogen-containing compound which is a suitable source of assimilable nitrogen for metabolic utilization by the microorganism selected. Suitable organic nitrogen sources can include, for example, protein, protein hydrolysates, amino acids, urea, and the like. Suitable inorganic nitrogen sources can include, for example, ammonia, ammonium hydroxide, ammonium nitrate, ammonium sulfate, and the like. The presently preferred nitrogen source is ammonia which can be obtained from any suitable source.

When using the nutrient medium described above the source of assimilable nitrogen can be supplied by the separate addition of anhydrous ammonia ($NH_3$) to the fermentation vessel. The amount of $NH_3$ added will depend upon the pH desired for the reaction mixture. Without any added $NH_3$ the pH will be about 2, for the nutrient medium. When yeasts or fungi are utilized in the fermentation process, the pH is preferably in the range of about 3 to about 5 and for the utilization of bacteria, the pH should preferably be in the range of about 6 to about 7.5.

The fermentation reaction is an aerobic process wherein the oxygen needed for the process can be supplied from a free oxygen-containing source such as air which is suitably supplied to the fermentation vessel at a pressure of from approximately 1-100 atmospheres and preferably from about 1 to about 10 atmospheres. Suitable sources of oxygen are air or oxygen enriched air. The fermentation reaction is often favorably affected by use of enhanced pressure within the above-described broad and preferred ranges.

A heat labile micronutrient source stream is added to a feedstream, for example methanol, and filtered, for example, by one or more cartridge filters having pore sizes of preferably 1 micron or less to provide a sterile carbon and energy source stream containing heat labile vitamins or other heat labile micronutrients. As previously indicated, certain microorganisms require vitamins and/or other micronutrients which may be heat labile for optimal growth. Examples are previously mentioned yeasts which appear to require the presence of one or both of the vitamins biotin and thiamine for their proper propagation. These heat labile micronutrients may be chemically sterilized, for example by contact with an alcohol such as methanol, or preferably mechanically sterilized, as by filtration through one or more cartridge filters, such as by sequential filtration through a pair of cartridge filters, the first having a pore size of from about 0.5 to about 1 micron and the second a pore size of around 0.2 micron, for the purpose of removing contaminating organisms so as to prevent loss of efficacy of the heat labile micronutrients and/or contamination of the fermentor.

A typical example of biotin and thiamine containing source stream is as follows:

| Component | Amount |
|---|---|
| Biotin | 0.16 gm |
| Thiamine | 16.0 gm |
| 20% Methanol (aqueous) | 1000 mL |

Preferably the fermentation process of the instant invention is a continuous type but it is to be noted that it can be conducted as a batch process. In the continuous or batch process modes of operation the fermentation reactor is first sterilized and subsequently inoculated with a culture of the desired microorganism in the presence of all the required nutrients including oxygen and the carbon source. In the continuous method of operation the oxygen source or air is continuously introduced along with continuous introduction of nutrient medium, nitrogen source (if added separately) and alcohol at a rate which is either predetermined or in response to need which can be determined by monitoring such things as alcohol concentration, dissolved oxygen, and oxygen or carbon dioxide in the gaseous effluent from the fermentor. The feed rate of the various materials can be varied so as to obtain as rapid a cell growth as possible consistent with efficient utilization of the alcohol feed, i.e., a high yield of cell weight per weight of alcohol feed charged.

The fermentation process in the first fermentor 6 of the present invention can be carried out without restriction as to productivity. By feeding the essentially cell free broth of fermentor 6 into fermentor 30, as described above with reference to FIG. 1, no waste water disposal requirements are encountered from the first fermentor. By alternately feeding sterilized cell containing effluent of fermentor 6 into fermentor 30, as described above with reference to FIG. 2, waste water disposal requirements from the first fermentor are also avoided. The fermentation process of the second fermentor is preferably a high cell density process since by conducting the fermentation at high cell densities, that is, greater than at least about 80 grams of cells per liter of effluent (g/L), the effluent stream 32 of the second fermentor 30 can be subjected directly to typical drying means such as drum drying or spray drying, thereby virtually eliminating waste water disposal requirements for the integrated process. Thus, a first fermentation process, which is carried out at any suitable level of productivity, is made economically amenable to direct, simple workup by direct drying afforded previously only to fermentation processes which are carried out at high cell densities. Preferably the cell density of the second fermentation process is at least 80 g/L, and preferably between about 80 and about 160 g/L or even greater for high productivity. Since fermentation using bacterial microorganisms has not generally been as successful in operating at high cell density conditions as has fermentation employing yeast microorganisms, it is presently preferred to use a high cell density yeast fermentation process in the second fermentor 30.

As is known in the art, the feed rate of the alcohol is an important variable to control since in high concentration this material can actually inhibit cell growth and may even kill the microorganism. Therefore, the feed rate of the alcohol is adjusted such that the alcohol is consumed by the microorganism at essentially the same rate as it is being fed to the fermentor. There will preferably be little or no alcohol in the effluent which is continuously withdrawn from the fermentor in a continuous type of process. However, satisfactory operation can be achieved with up to about 0.5 percent by volume alcohol concentration in the effluent. For high cell productivity or growth rate, the concentration of alcohol in the feed to the fermentor should be from about 7 percent up to about 50 percent by volume.

For batch or continuous operation of the process of this invention, the concentration of feedstock, e.g., methanol, in the fermentor should be within the range of from 0.001 up to about 5 percent by volume (v/v) and preferably from 0.002 up to about 0.5 percent (v/v). It is possible, of course, and may in some instances be desirable, to add the feedstock incrementally to an otherwise typical batch fermentation process.

It is known in the art that instrumentation is available to measure cell density, pH, dissolved oxygen and alcohol concentration in the fermentor as well as the feed and effluent streams so as to provide a rather complete monitoring of the fermentation process with the instrumentation being adapted to control the input rates so as to optimize the process. The materials fed to the fermentor are preferably subjected to sterilization as is normally done in the art in order to prevent contamination of the desired fermentation mixture by unwanted viable microorganisms.

In the disclosed embodiment a concentrated fresh medium stream is combined with the effluent stream of the first fermentor and the combined stream is sterilized in a sterilizer such as, for example, a steam sterilizer as is known in the art. In accordance with the present invention, the concentrated fresh media can be added either to a hold tank functioning in addition as a make-up tank or can be combined with a portion of an effluent stream from the hold tank, for example. In either event the combined stream is then sterilized, cooled, and introduced into the fermentor 30. The combined stream is cooled by means of a cooler such as an indirect shell-tube heat exchanger or by other suitable means as are known in the art. For fuel economy the separator effluent stream and/or a stream comprising at least a portion of the fluid stored in the hold tank can be used as a cooling fluid to remove heat from the sterilized medium-enhanced effluent stream and the heated effluent stream returned to the hold tank to assist maintaining the temperature of the stored fluid in the hold tank at an inhibitory temperature sufficient to inhibit the growth of most microorganisms. Alternatively a hold tank 21 can have cooling coils or other high transfer area indirect heat exchange means mounted directly therein and have the sterilized fluid from a sterilizer 25 pass therethrough to simultaneously cool the sterilized fluid and heat the hold fluid in hold tank 21. Additional cooling means can be added downstream of the hold tank 21 as required to cool the sterilized fluid stream 26 sufficiently for use in fermentor 30. Also, as shown in FIGS. 1 and 2, a hold tank 21 can have means such as a steam jacket 20 into which steam is injected to maintain the temperature of the hold tank 21 under growth inhibiting conditions effective to inhibit microorganism growth.

As used herein, "growth inhibiting conditions" refers to conditions effective to inhibit vegetative growth of microorganisms. Growth inhibiting conditions are thus distinguished from sterilizing conditions. Sterilizing conditions are selected to insure the death of the most resistant microbial form present. Vegetative microbial cells and vegetative growth are accordingly not the primary concern in sterilization. Resistant forms such as microbial spores typically dictate the sterilizing conditions required. Some of the more resistant microbial spores can survive boiling for many hours and it can be necessary to go to higher temperatures under steam pressure to kill them in a reasonably short period of time.

Growth inhibiting conditions, however, are primarily concerned with the vegetative or growth forms of the microbial cells. It is these cells which can proliferate in an effluent stream causing accumulation of undesirable cells or byproducts.

Growth inhibiting conditions comprise a temperature effective to inhibit growth of microoganisms. Preferably, the temperature is in the range of about 65° C. (150° F.) to about 82° C. (180° F.) since temperatures in this range are effectively growth inhibiting for most microorganisms. More preferably, the temperature is in the range of about 70° C. (158° F.). These ranges are suitable for assuring inhibition of most unwanted microbial growth consistent with good heat and energy economy. Heat lost during the cooling step after heat sterilization can be effectively used to inhibit microbial growth in the effluent stream of the first fermentor. Although thermophilic microorganisms are rarely encountered which can grow at these temperature ranges, the preferred ranges are effectively growth inhibiting for most usually encountered microorganisms and if contaminating thermophilic microorganisms are occasionally encountered, the hold temperature effective for growth inhibition can be readily determined by one skilled in the art.

The hold tank 21 can also function as a surge tank. In a continuous or bath SCP production process, some process surge is necessary in order to contend with various fluctuations in feed rates and amounts which occur. By maintaining the surge volume at an inhibitory temperature nutrient loss and accumulation of contamination products is prevented while fuel economy is promoted relative to a system in which the entire surge volume, which can be very large, is sterilized.

A portion of the stored fluid in the hold tank is combined with a concentrated fresh media stream and the combined stream is then sterilized, for example, in a steam sterilizer or other suitable heat sterilizers as are known in the art to produce a sterilized medium-enhanced effluent stream which is cooled as hereinabove described and introduced into a fermentor 30. In such sterilizers the fluid to be sterilized is first passed through a heating coil at between approximately 115° C. and 125° C. and thence passed to a hold tank where the fluid is held for a residence time to insure complete sterilization. Any suitable sterilization means can be used, however.

The fermentation process in fermentor 30 is carried out at high cell density conditions, as are taught in the art. The effluent broth from fermentor 30 is subjected directly to direct drying procedures. Thus, the effluent media from a first fermentor is efficiently utilized by a second fermentor which, by virtue of producing single cell protein product at high cell density, thereby allows economical recovery of SCP product by direct drying and producing essentially no waste water from the integrated process.

While the invention has been described herein in conjunction with preferred embodiments herein, reasonable variations and modifications by those skilled in the art are considered to be within the scope of the foregoing description of the invention and the appended claims thereto.

What is claimed is:

1. A process for producing a cellular product comprising:
    (a) withdrawing a fermentation effluent from a first fermentation zone;
    (b) subjecting said fermentation effluent to sterilizing conditions to produce a sterilized fermentation effluent;
    (c) utilizing said sterilized fermentation effluent as at least a portion of the nutrient media for a high cell density fermentation process conducted within a high cell density fermentation zone;
    (d) removing a stream containing microbial cells from said high cell density fermentation zone; and
    (e) drying said stream containing microbial cells to produce a dried cellular product.

2. A process according to claim 1 further comprising removing a cellular product from said sterilized fermentation effluent in claim 1 (b) before said sterilized fermentation effluent is used as at least a portion of the nutrient media in a high cell density fermentation process.

3. A process according to claim 1 further comprising adding nutrient material to said sterilized fermentation effluent before said stream is passed to said high cell density fermentation zone.

4. A process according to claim 1 wherein said first fermentation zone employs bacteria and said high cell density fermentation zone employs yeast.

5. A process according to claim 1 wherein said high cell density fermentation zone contains at least about 80 grams of microbial cells per liter of fermentation effluent.

6. A process according to claim 5 wherein said high cell density fermentation zone contains between about 80 and about 160 grams of microbial cells per liter of fermentation effluent.

* * * * *